United States Patent [19]

Blanchard

[11] Patent Number: 5,095,107
[45] Date of Patent: Mar. 10, 1992

[54] PROCESS FOR CLEAVAGE OF ESTERS DURING THE PRODUCTION OF CEPHALOSPORINS

[75] Inventor: William B. Blanchard, Indianapolis, Ind.

[73] Assignee: Eli Lilly and Company, Indianapolis, Ind.

[21] Appl. No.: 608,772

[22] Filed: Nov. 5, 1990

[51] Int. Cl.$^5$ .............................................. C07D 501/04
[52] U.S. Cl. .................................. 540/205; 540/215; 540/221; 540/222; 540/230
[58] Field of Search ............... 540/222, 230, 215, 221, 540/205

[56] References Cited

U.S. PATENT DOCUMENTS 5,043,439  8/1991  Kant et al. .......................... 540/215

OTHER PUBLICATIONS

Dean, P., *J. Chem. Soc.*, Halogenolysis of Methyl Glycyrrhetate with Lithium Iodide–Dimethylformamide, (1965) p. 6655.

Elsinger et al., *Helv. Chim. Acta*, vol. XLIII, No. 14–15 (1960) pp. 113–118.

McMurry et al., *Synthetic Communications* 2(6), 389–394 (1972) An Improved Method for the Cleavage of Methyl Esters.

Mochida et al., *Chem. Pharm. Bull.*, vol. 36 (1988) pp. 3642–3645, Synthetic Studies on 1-Carbacephem Antibiotics: New Synthetic Approach to 3H-Carbacephems.

*Primary Examiner*—Nicholas S. Rizzo
*Attorney, Agent, or Firm*—Joseph A. Jones; Leroy Whitaker

[57] ABSTRACT

Superior method for the removal of the methyl or ethyl ester group from cephalosporin and carbacephalosporin carboxylic acids.

20 Claims, No Drawings

PROCESS FOR CLEAVAGE OF ESTERS DURING THE PRODUCTION OF CEPHALOSPORINS

BACKGROUND OF THE INVENTION

This invention belongs to the field of organic chemistry and the synthesis of cephalosporin antibiotics. The invention provides a superior method for removal of the methyl or ethyl ester group from cephalosporin and carbacephalosporin carboxylic acids. The process is economically important, because cephalosporin antibiotics are often processed in the form of an ester. The methyl and ethyl esters are convenient and economical to handle in chemical processing, however, such esters have been seldom used due to the difficulty in their removal. The ester group must eventually be removed, however, because the cephalosporins are used as pharmaceuticals in the acid or salt form.

STATE OF THE ART

Many types of protecting groups have been proposed and used for carboxylic acids. The standard textbook, Protective Groups in Organic Chemistry, Plenum Press, N.Y., 1973, J. F. W. McOmie, Ed., devotes chapter 5 to the subject. Simple esters have been proposed as carboxyl protecting groups, however, the cephalosporin chemist has seldom used the methyl or ethyl esters due to the harsh deesterification process.

The protective group must be selectively removed in good yield by readily available reagents, which do not attack the regenerated functional group. Traditional methyl or ethyl deesterification methods require harsh acids such as trifluoroacetic acid, with the attendant disadvantage that the deesterification may affect functional groups of the molecule other than the simple ester. The art suggests that simple ester carboxyl protecting groups are undesirable for cephalosporin manufacture due to harsh deesterification conditions and purification concerns. Flynn, Cephalosporins and Penicillins, at 172 (Academic Press, New York, 1972).

This invention is a mild deesterification process which minimizes decomposition of the cephalosporin compounds. Additionally, the process provides one-step separation and purification of the pharmaceutically acceptable product.

SUMMARY OF THE INVENTION

This invention provides a process for preparing a compound of the formula (I)

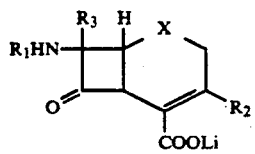

(I)

wherein
X is $CH_2$ or sulfur;
$R_1$ is hydrogen, an amino protecting group, or an acyl group

wherein R is hydrogen, $C_1$-$C_6$ alkyl, $C_1$-$C_6$ alkyl substituted by cyano, carboxy, halogen, amino, $C_1$-$C_4$ alkoxy, $C_1$-$C_4$ alkylthio, trifluoromethyl, or trifluoromethylthio, naphthyl, an optionally substituted phenyl group represented by the formula

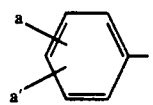

wherein a and a' independently are hydrogen, halogen, hydroxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, hydroxymethyl, aminomethyl, or carboxymethyl; a group represented by the formula

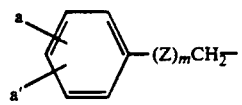

wherein Z is O or S, and m is 0 or 1; a heteroarylmethyl group represented by the formula

wherein $R_6$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, or $C_1$-$C_4$ alkylsulfonylamino; a substituted methyl group represented by the formula

wherein $R_7$ is cyclohex-1,4-dienyl, or an optionally substituted phenyl group represented by the formula

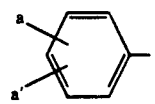

wherein a and a' have the above defined meanings, or $R_7$ is $R_6$ as defined above, and Q is hydroxy, $C_1$-$C_4$ alkanoyloxy, carboxy, sulfo, or amino; or R is a keto group or an oximino-substituted group represented by the formula

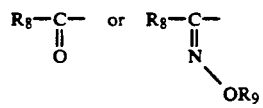

wherein $R_8$ is $R_6$ or $R_7$ as defined above and $R_9$ is hydrogen, $C_1$-$C_4$ alkyl, or a carboxy-substituted alkyl or cycloalkyl group represented by the formula

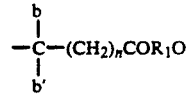

wherein b and b' independently are hydrogen or $C_1-C_3$ alkyl, or b and b', when taken together with the carbon to which they are bonded, form a 3- to 6-membered carbocyclic ring, n is 0-3, and $R_{10}$ is hydroxy, $C_1-C_4$ alkoxy, amino, $C_1-C_4$ alkylamino, or di($C_1-C_4$alkyl)amino;

$R_2$ is chlorine, bromine, or methyl;

$R_3$ is hydrogen, $C_1-C_4$ alkoxy, $C_1-C_4$ alkylthio, or formamido; which process comprises contacting a substrate of the formula

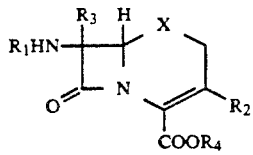

wherein $R_4$ is methyl or ethyl;

with LiI in a reaction mixture containing a substantial concentration of acetonitrile. Product may be isolated from the reaction medium by simple filtration. The process minimizes decomposition of the pharmaceutically desirable product and facilitates purification.

DESCRIPTION OF THE PREFERRED EMBODIMENTS

The compounds of the type prepared by the process of this invention are known in the cephalosporin art. No new compounds are provided by the present invention. To assure that the reader understands the compounds, and understands the esters which are the starting compounds used in the present invention, some discussion and explanation of the formulae will be given.

In the above general formula, various generalized terms are used to describe the numerous groups. The generalized terms have their usual meanings in organic chemistry.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl, and iodoacetyl groups, urethane-type blocking groups such as benzyloxycarbonyl, 4-phenylbenzyloxycarbonyl, 2-methylbenzyloxycarbonyl, 4-methoxybenzyloxycarbony-1,4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 1,1-diphenyleth-1-yloxycarbonyl, cyclopentanyloxycarbonyl, 1-methylcyclopentanyloxycarbonyl, cyclohexanyloxycarbonyl, 1-methoxycyclohexanyloxycarbonyl, 2-methylcyclohexanyloxycarbonyl, 2-(4-tolylsulfonyl)ethoxycarbonyl, 2-(methylsulfonyl)-ethoxycarbonyl, 2-(triphenylphosphino)ethoxycarbonyl, 9-fluorenylmethoxycarbonyl ("FMOC"), 2-(trimethylsilyl)-ethoxycarbonyl, allyloxycarbonyl, 1-(trimethylsilylmethyl)prop-1-en-3-yloxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, 1-piperidyloxycarbonyl and the like; the benzoylmethylsulfonyl group, the 2-(nitro)-phenylsulfonyl group, the diphenylphosphine oxide and like amino-protecting groups. Preferred amino-protecting groups are the 1,2-bis-(dimethylsilyl)ethylene (See, e.g., U.S. Pat. No. 4,558,124), benzyloxycarbonyl, p-nitrobenzyloxycarbonyl, allyloxycarbonyl, t-butoxycarbonyl, and trityl groups. Similar amino-protecting groups used in the cephalosporin, penicillin and peptide art are also embraced by the above term. Further examples of groups referred to by the above terms are described by J. W. Barton, Protective Groups in Organic Chemistry, at ch. 7 (J. G. W. McOmie Ed.) (Plenum Press, New York, 1981).

In the above definition of the compounds, "$C_1-C_6$ alkyl" refers to the straight and branched chain alkyl groups such as methyl, ethyl, n-propyl, isopropyl, butyl and like alkyl groups; "$C_1-C_6$ alkyl substituted by . . . carboxy" refers to such groups as carboxymethyl, 2-carboxyethyl, 2-carboxypropyl, 4-carboxybutyl, 5-carboxypentyl, and the like; "$C_1-C_6$ alkyl substituted by . . . halogen" refers to chloromethyl, bromomethyl, 2-chloroethyl, 1-bromoethyl, 4-chlorobutyl, 4-bromopentyl, 6-chlorohexyl, 4-fluorobutyl, fluoromethyl, and the like; "$C_1-C_6$ alkyl substituted by . . . amino" refers to such groups as 2-aminoethyl, aminomethyl, 3-aminopropyl and 4-aminobutyl;" $C_1-C_6$ alkyl substituted by . . . $C_1-C_4$ alkoxy" refers to methoxymethyl, 2-methoxyethyl, 2-ethoxyethyl, ethoxymethyl, 3-propoxypropyl, 4-t-butoxybutyl, 3-methoxypentyl, 6-methoxyhexyl, and like groups; "$C_1-C_6$ alkyl substituted by . . . $C_1-C_4$ alkylthio" refers to such groups as methylthiomethyl, 2-methylthioethyl, 2-ethylthiopropyl, 3-t-butylthiopropyl, and like groups; "$C_1-C_6$ alkyl substituted by . . . trifluoromethyl" is exemplified by 2,2,2-trifluoroethyl, 3,3,3-trifluoropropyl, 4,4,4-trifluorobutyl, 6,6,6-triflurohexyl, and the like; and $C_1-C_6$ alkyl substituted by . . . trifluoromethylthio" refers to such groups as trifluoromethylthiomethyl, 2-trifluoromethylthiopropyl, 4-trifluoromethylthiobutyl, 5-trifluoromethylthiohexyl, and like $C_1-C_6$ alkyl substituted groups.

The term "halogen" refers to the fluoro, chloro, bromo, or iodo groups.

When, in the formula I, R is a substituted phenyl group wherein the substituent(s) are represented by a and a', examples of such groups are halophenyl such as 4-chlorophenyl, 3-bromophenyl, 2-fluorophenyl, 2-iodophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butoxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylaminophenyl such as 2-acetylaminophenyl, 4-acetylaminophenyl, 3-propionylaminophenyl, and 4-butyrylaminophenyl; alkylsulfonylaminophenyl such as 3-methylsulfonylaminophenyl, 4-methylsulfonylaminophenyl, 3,5-di(methylsulfonylamino)phenyl, 4-n-butylsulfonylaminophenyl, and 3-ethylsulfonylaminophenyl; carboxyphenyl such as 2-, 3-, or 4-carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4-di(carboxymethyl)phenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCO- groups of the formula I wherein R is a group represented by the formula

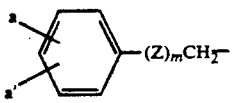

with m=0 are: phenylacetyl, 4-hydroxyphenylacetyl, 4-chlorophenylacetyl, 3,4-dichlorophenylacetyl, 4-methoxy-phenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=O, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R_6$—$CH_2CO$—groups of the formula I wherein $R_6$ is a heteroaryl group are: 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, and like heteroaryl groups substituted by amino, $C_1$–$C_4$ alkylsulfonylamino, hydroxy, halo, $C_1$–$C_4$ alkyl or $C_1$–$C_4$ alkoxy groups.

Examples of RCO- groups of the formula I compounds wherein R is a substituted methyl group represented by the formula $R_7$—CH(Q)—wherein Q is amino, carboxy, hydroxy, or sulfo, are 2-carboxy-2-phenylacetyl, 2-amino-2-(2-naphthalenyl)acetyl, 2-carboxy-2-(4-hydroxyphenyl)-acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-amino-2-(3-methylsulfonamidophenyl)acetyl, 2-amino-2-(3-ethylsulfonaminophenyl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)-acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl.

Examples of RCO acyl groups of the compounds represented by formula I when R is a keto group or an oximino-substituted group represented by the formulae

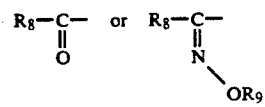

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyaminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothia-zol-4-yl)-2-(2-carboxyprop-2-yl)oxyiminoacetyl, 2-(2-aminothiazol-4-yl)-2-(2-carbamoylprop-2-yl)oxyiminoacetyl, and 2-(5-amino-1,3,4-thiadiazol-2-yl)-2-methoxyiminoacetyl.

Examples of the above defined cephalosporins and carbacephalosporins are described below in Table 1 where-in the terms in the column headings refer to formula (I). Compounds illustrated in the table are products of this process. The corresponding substrate may be the ethyl or methyl ester of the product.

| $R_1$ | $R_2$ | $R_3$ | X |
|---|---|---|---|
| acetyl | methyl | hydrogen | $CH_2$ |
| n-propionyl | chlorine | methoxy | sulfur |
| t-butyryl | bromine | ethoxy | $CH_2$ |
| n-valeryl | methyl | isopropoxy | sulfur |
| 3-methoxyvaleryl | chlorine | n-butoxy | $CH_2$ |
| cyanoacetyl | bromine | methylthio | sulfur |
| 4-cyanobutyryl | methyl | ethylthio | $CH_2$ |
| 2-carboxyacetyl | chlorine | isopropylthio | sulfur |
| 4-carboxybutyryl | bromine | n-butylthio | $CH_2$ |
| chloroacetyl | methyl | isobutylthio | sulfur |
| bromoacetyl | chlorine | formamido | $CH_2$ |
| 4-fluorobutyryl | bromine | hydrogen | sulfur |
| 6-chlorohexanoyl | methyl | methoxy | $CH_2$ |
| 2-aminoacetyl | chlorine | ethoxy | sulfur |
| 4-aminobutyryl | bromine | hydrogen | $CH_2$ |
| methoxyacetyl | methyl | methoxy | sulfur |
| ethoxyacetyl | chlorine | ethoxy | $CH_2$ |
| 6-methoxyhexanoyl | bromine | isopropoxy | sulfur |
| methylthioacetyl | methyl | n-butoxy | $CH_2$ |
| 2-ethylthiopropionyl | chlorine | methylthio | sulfur |
| 3-t-butylthiopropionyl | bromine | ethylthio | $CH_2$ |
| 2,2,2-trifluoroacetyl | methyl | isopropylthio | sulfur |
| 4,4,4-trifluorobutyryl | chlorine | n-butylthio | $CH_2$ |
| 4-chlorophenylacetyl | bromine | isobutylthio | sulfur |
| 3-bromophenylacetyl | methyl | formamido | $CH_2$ |
| 2,4-dichlorophenylacetyl | chlorine | hydrogen | sulfur |
| 2-hydroxyphenylacetyl | bromine | methoxy | $CH_2$ |
| 4-hydroxyphenylacetyl | methyl | ethoxy | sulfur |
| 3,4-dihydroxyphenylacetyl | chlorine | isopropoxy | $CH_2$ |
| 2,6-dimethoxyphenylacetyl | bromine | n-butoxy | sulfur |
| 4-methoxy-3-ethoxyphenylacetyl | methyl | methylthio | $CH_2$ |

| R₁ | R₂ | R₃ | X |
|---|---|---|---|
| 2-acetoxyphenylacetyl | chlorine | ethylthio | sulfur |
| 4-formyloxyphenylacetyl | bromine | isopropylthio | $CH_2$ |
| 3-butyryloxyphenylacetyl | methyl | n-butylthio | sulfur |
| 4-methylphenylacetyl | chlorine | isobutylthio | $CH_2$ |
| 3-t-butylphenylacetyl | bromine | formamido | sulfur |
| 4-ethyl-3-methylphenylacetyl | methyl | hydrogen | $CH_2$ |
| 4-methylthiophenylacetyl | chlorine | methoxy | sulfur |
| 3-n-butylthiophenylacetyl | bromine | ethoxy | $CH_2$ |
| 3,4-di(methylthio)phenylacetyl | methyl | isopropoxy | sulfur |
| 2-aminophenylacetyl | chlorine | n-butoxy | $CH_2$ |
| 3,5-diaminophenylacetyl | bromine | methylthio | sulfur |
| 2-acetylaminophenylacetyl | methyl | ethylthio | $CH_2$ |
| 3-propionylaminophenylacetyl | chlorine | isopropylthio | sulfur |
| 3,5-di(methylsulfonylamino)phenylacetyl | bromine | n-butylthio | $CH_2$ |
| 3,4-dicarboxyphenylacetyl | methyl | isobutylthio | sulfur |
| 4-carboxyphenylacetyl | chlorine | formamido | $CH_2$ |
| 2-carbamoylphenylacetyl | bromine | hydrogen | sulfur |
| 2,4-dicarbamoylphenylacetyl | methyl | methoxy | $CH_2$ |
| 4-hydroxymethylphenylacetyl | chlorine | ethoxy | sulfur |
| 2-aminomethylphenylacetyl | bromine | isopropoxy | $CH_2$ |
| 2-carboxymethylphenylacetyl | methyl | n-butoxy | sulfur |
| 3,4-di(carboxymethyl)-phenylacetyl | chlorine | methylthio | $CH_2$ |
| 4-chloro-3-methyl-phenylacetyl | bromine | ethylthio | sulfur |
| 4-hydroxy-3-chloro-phenylacetyl | methyl | isopropylthio | $CH_2$ |
| 3-ethyl-4-hydroxy-phenylacetyl | chlorine | n-butylthio | sulfur |
| 4-t-butoxy-2-hydroxy-phenylacetyl | bromine | isobutylthio | $CH_2$ |
| 3-amino-2-ethylphenylacetyl | methyl | formamido | sulfur |
| 2-hydroxymethyl-4-fluorophenylacetyl | chlorine | hydrogen | $CH_2$ |
| 2-acetoxy-4-aminophenylacetyl | bromine | methoxy | sulfur |
| 3-isopropylthio-4-chloro-phenylacetyl | methyl | ethoxy | $CH_2$ |
| phenylacetyl | bromine | ethoxy | $CH_2$ |
| 3-hydroxyphenylacetyl | methyl | isopropoxy | sulfur |
| 3,4-dichlorophenylacetyl | chlorine | n-butoxy | $CH_2$ |
| 4-methoxyphenylacetyl | bromine | methylthio | sulfur |
| 3-aminomethylphenylacetyl | methyl | ethylthio | $CH_2$ |
| 4-acetoxyphenylacetyl | chlorine | isopropylthio | sulfur |
| 4-acetylaminophenylacetyl | bromine | n-butylthio | $CH_2$ |
| phenoxyacetyl | methyl | isobutylthio | sulfur |
| 4-fluorophenoxyacetyl | chlorine | formamido | $CH_2$ |
| 3-aminophenoxyacetyl | bromine | hydrogen | sulfur |
| 2-methylthiophenoxyacetyl | methyl | methoxy | $CH_2$ |
| phenylthioacetyl | chlorine | ethoxy | sulfur |
| 2-fluorophenylthioacetyl | bromine | isopropoxy | $CH_2$ |
| 2-thienylacetyl | methyl | n-butoxy | sulfur |
| 2-furylacetyl | chlorine | methylthio | $CH_2$ |
| 2-benzothienylacetyl | bromine | ethylthio | sulfur |
| indol-2-ylacetyl | methyl | isopropylthio | $CH_2$ |
| 1H-tetrazol-1-ylacetyl | chlorine | n-butylthio | sulfur |
| oxazol-4-ylacetyl | bromine | isobutylthio | $CH_2$ |
| thiazol-4-ylacetyl | methyl | n-butylthio | sulfur |
| 5-ethyl-1,3,4-thiadiazol-2-ylacetyl | chlorine | isobutylthio | $CH_2$ |
| 2-carboxy-2-phenylacetyl | bromine | formamido | sulfur |
| 2-amino-2-(4-hydroxyphenyl)-acetyl | methyl | hydrogen | $CH_2$ |
| 2-amino-2-(3-ethylsulfonyl-aminophenyl)acetyl | chlorine | methoxy | sulfur |
| 2-amino-2-(4-methylphenyl)-acetyl | bromine | ethoxy | $CH_2$ |
| 2-amino-2-(benzothien-3-yl) | methyl | isopropoxy | sulfur |
| 2-hydroxy-2-(1,3,4-thiadiazol-2-yl)-acetyl | chlorine | n-butoxy | $CH_2$ |
| 2-carboxy-2-(benzothien-2-yl)acetyl | bromine | methylthio | sulfur |
| 2-oxo-2-phenylacetyl | methyl | ethylthio | $CH_2$ |
| 2-(2-chlorothiazol-4-yl)-2-methoxyiminoacetyl | chlorine | isopropylthio | sulfur |
| 2-(2-thienyl)-2-ethoxyimino-acetyl | bromine | n-butylthio | $CH_2$ |
| 2-oxo-2-(2-aminothiazol-4-yl)acetyl | methyl | isobutylthio | sulfur |
| 2-(2-aminothiazol-4-yl)-2-(2-carbamoyl-prop-2-yl)oxyiminoacetyl | chlorine | formamido | $CH_2$ |
| acetyl | bromine | hydrogen | sulfur |
| n-propionyl | methyl | methoxy | $CH_2$ |
| t-butyryl | chlorine | ethoxy | sulfur |
| n-valeryl | bromine | isopropoxy | $CH_2$ |

All of the compounds of the formula type above are known in the literature of the cephalosporin art, although the simple esters of some of the compounds may not necessarily have been specifically described. Formation of simple esters of cephalosporin acids is a routine expedient in the art, however, as taught by Chauvette, R. R., et al., Antimicrobial Agents and Chemotherapy-1962, 687 (Robert Day et al., ed.) (American Society for Microbiology, 1963). The simple esters are usually formed at a relatively early stage in the synthesis of the cephalosporin, and the compound is carried through synthetic steps in the simple ester form. It may be advantageous to form the simple ester of a penicillin, especially a penicillin 1-oxide, and transform the penicillin into a cephalosporin by one of the well-known ring expansion techniques. The cephalosporin ester so made may then be subjected to additional steps to form the desired compound, and finally deesterified by the process of this invention to obtain the antibiotically active cephalosporin acid.

Certain classes of the compounds described by the formula above are preferred for use in the process of this invention, and certain conditions of operating the process are preferred conditions. The listing below shows the preferred conditions and substrate in tabular form. It will be understood that the various preferred conditions and substrates may be combined to create other, more limited preferred modes of the invention.

(a) $R_1$ is hydrogen;
(b) $R_1$ is phenylglycine or substituted phenylglycine;
(c) $R_1$ is phenoxyacetyl;
(d) $R_1$ is thienylacetyl;
(e) $R_1$ is acetyl;
(f) $R_2$ is chlorine;
(g) $R_2$ is methyl;
(h) $R_3$ is hydrogen;
(i) $R_4$ is methyl;
(j) $R_4$ is ethyl;
(k) X is $CH_2$;
(l) X is sulfur;
(m) The reaction medium is substantially pure acetonitrile;
(n) The reaction medium is comprised of from about 0-20% aprotic solvent and from about 80%-100% acetontrile;
(o) The reaction medium is comprised of from about 0-20% dimethyl sulfoxide and from about 80-100% acetonitrile;
(p) The amount of lithium iodide is from about 2 mole to about 7 mole per mole of product to be produced;
(q) The amount of lithium iodide is about 3 mole per mole of product to be produced.

The term aprotic solvent refers to polar solvents of moderately high dielectric constant which do not contain an acidic hydrogen. Examples of common aprotic solvents are dimethyl sulfoxide (DMSO), dimethyl-formamide or sulfolane.

A particularly preferred class of products of the present process includes those compounds wherein X is $CH_2$; $R_1$ is hydrogen, phenoxyacetyl, substituted phenylglycine (particularly p-hydroxy substituted phenylglycine), or phenylglycine; $R_2$ is Cl.

The process of this invention will now be explained in detail. It will be observed that the process is appropriate for large scale equipment, and that none of the intermediates, reagents or solvents present any unusual hazards of flammability or toxicity. The equipment needed to carry out the process is of the types commonly found in organic chemical processing plants.

The concentration of the reaction mixture is not critical.

No exact times are given for the process. As is always the case in chemistry, the speeds of the reactions depend closely on the operation temperatures, and in part on other considerations such as the exact compound which is to be prepared. Indications of time are given below for the guidance of the reader, who will understand that the times stated are only indications of the preferred conditions and that the times will vary markedly under slightly different operating conditions. An organic chemist will understand that the course of the reaction can be easily followed, as by thin layer chromatography or high pressure liquid chromatography, to detect when the reaction is as complete as desired. The operator may maximize the yields of the process by giving maximum periods of reaction time or may wish to maximize throughput by cutting off the reaction at the point where it has reached an economical degree of completion.

All of the starting materials and reagents used in the process of this invention are well known to organic chemists, and can easily be purchased or prepared by established methods in the art.

The methyl or ethyl ester of the compounds described above is contacted with an excess of lithium iodide in a medium of a substantial concentration of acetonitrile.

An excess from about 2 mole to about 7 mole lithium iodide per mole of desired product is the preferred embodiment. Molar excess of about three is the most preferred ratio of lithium iodide to product.

The reaction medium is substantially comprised of acetonitrile. The reaction medium may be a mixture comprised of acetonitrile and a lesser amount of an aprotic solvent. An acceptable blend is from about 80-100% acetonitrile and from about 0-20% aprotic solvent. Reaction medium of substantially pure acetonitrile is the most preferred embodiment. "Substantially pure acetonitrile" refers to acetonitrile of the usual commercially available purity.

The mixture may be heated above ambient temperature to accomplish the deesterification. The process is preferably carried out at moderately elevated temperatures from about 40° C. to about 100° C. It is usually convenient to operate at the reflux temperature of the reaction mixture, which temperature may be adjusted in the usual manner by putting the reaction mixture under pressure or under vacuum to raise or lower the reflux temperature as may be convenient in a given instance. Operation under pressure is necessary if a temperature above the boiling point of the mixture is used.

When the deesterification process has gone to the desired degree of completion, the product lithium salt of the substrate is isolated from the reaction medium. A number of expedients may be utilized. For example, the solid lithium salt may be isolated by simple filtration methods, including filtration by sand, sintered glass, porous membrane, or paper. Alternatively, the product may be recovered by centrifugation. The most preferred isolation method is simple filtration using porous membrane, sintered glass, or paper.

No further purification of the product is necessary. The process of this invention provides a product of pharmaceutically acceptable purity.

Optionally, the lithium salt, which is a useful antimicrobial, may be converted to the zwitterionic or acid form of the cephalosporin by known methods.

The Examples below are shown to assure that chemists can utilize the process disclosed in this invention.

In the following Examples, the term nuclear magnetic resonance spectra has been abbreviated NMR. In conjunction with the NMR spectra, the following abbreviations are used: "s" is singlet, "d" is doublet, "m" is multiplet, and "DMSO-$d_6$" is dimethyl sulfoxide where all protons have been replaced with deuterium.

The NMR spectra were obtained on a General Electric QE-300 instrument. The chemical shifts are expressed in $\delta$ values (parts per million downfield from tetramethylsilane).

EXAMPLE 1

A 364 mg (1 mmole) portion of 7-((phenoxyacetyl)amino)-1-carba(dethia)-3-chloro-3-cephem-4-carboxylic acid, methyl ester was dissolved in a reaction medium comprised of 1.2 ml dimethyl sulfoxide (DMSO) and 4.8 ml acetonitrile ($CH_3CN$). A 0.8 g (6 mmole) portion of lithium iodide was ground with a mortar and pestle prior to being added to the cephalosporin solution. The mixture was heated to reflux and stirred at that temperature for six hours. A 1 ml portion of acetonitrile was added to the mixture and refluxing was continued over night.

The reaction product mixture was cooled in an ice bath for about one hours. The product was isolated by filtration and washed with cold acetonitrile (3 ml) and ether (1 ml). The solid product had a melting point of 225° C. The product was identified as the lithium salt of 7-((phenoxyacetyl)amino)-1-carba(dethia)-3-chloro-3-cephem-4-carboxylic acid by nuclear magnetic resonance spectrum and mass spectroscopy. The total yield of the compound was 280 mg. (78%).

$^1$H NMR (DMSO-$d_6$)$\delta$ 6.85–7.3 (m, 5H), $\delta$ 5.15 (m, 1H), $\delta$ 4.5 (s, 2H), $\delta$ 3.65 (m, 1H), $\delta$ 2.2–2.5 (m, 2H), $\delta$ 1.6–1.8 (m, 2H)

MS: m/e 350 (m+)

EXAMPLE 2

A process similar in every respect to Example 1 was completed with varying molar equivalents of lithium iodide. Molar excess of 1, 3, and 5 moles lithium iodide to desired product were investigated. The results are shown below.

| Mole LiI per mole product | Total Yield |
| --- | --- |
| 1 | 27% |
| 3 | 70% |
| 5 | 73% |

EXAMPLE 3

Preparation of the Acid Form

A 1.53 g. (4.2 mmole) portion of 7-((phenoxyacetyl)amino)-1-carba(dethia)-3-chloro-3-cephem-4-carboxylic acid, methyl ester was added to 15 ml of acetonitrile in a 100 ml. round bottom flask. The mixture was heated to reflux under a slow nitrogen purge. A 2.8 g (21 mmole) portion of lithium iodide was added to the mixture. The reaction mixture was heated to reflux for six hours and stirred over night at room temperature.

The next day 25 ml of water and 20 ml of ethyl acetate were added to the mixture. The reaction mixture was stirred for 20 minutes. The water layer was removed. The remaining organic layer was extracted with 20 ml of water. Sodium carbonate was added to aid in separation. The water layer was adjusted to pH 2 and extracted several times with methylene chloride. The methylene chloride layers were combined and stirred with Darco, magnesium sulfate, and sodium sulfate. The solution was filtered through fiber glass and pre-folded filter papers. The resulting clear solution was concentrated to a white solid. The product was identified as 7-((phenoxyacetyl)-amino)-1-carba(dethia)-3-chloro-3-cephem-4-carboxylic acid by N.M.R. spectrum. The total yield of the compound was 1.0 g (70%)

$^1$H NMR (DMSO-d$_6$) δ 8.9 (d, 1H), δ 6.9–7.3 (m, 5H), δ 5.4 (m, 1H), δ 4.55 (s, 2H), δ 3.82 (m, 1H), δ 2.5–2.65 (m, 2H), and δ 1.6–1.95 (m, 2H)

I claim:

1. A process for preparing a compound of the formula (I)

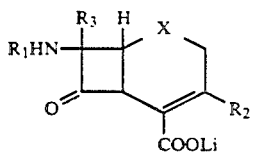

wherein
X is CH$_2$ or sulfur;
R$_1$ is hydrogen, an amino protecting group, or an acyl group

wherein R is hydrogen, C$_1$-C$_6$ alkyl, C$_1$-C$_6$ alkyl substituted by cyano, carboxy, halogen, amino, C$_1$-C$_4$ alkoxy, C$_1$-C$_4$ alkylthio, trifluoromethyl, or trifluoromethylthio, naphthyl, an optionally substituted phenyl group represented by the formula

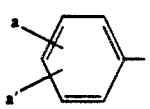

wherein a and a' independently are hydrogen, halogen, hydroxy, C$_1$-C$_4$ alkyl, C$_1$-C$_4$ alkylthio, amino, C$_1$-C$_4$ alkanoylamino, C$_1$-C$_4$ alkylsulfonylamino, carboxy, carbamoyl, hydroxymethyl, aminomethyl, or carboxymethyl; a group represented by the formula

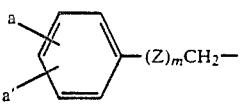

wherein Z is O or S, and m is 0 or 1;
a heteroarylmethyl group represented by the formula

wherein R$_6$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, C$_1$-C$_4$ alkyl, C$_1$-C$_4$ alkoxy, or C$_1$-C$_4$ alkylsulfonylamino; a substituted methyl group represented by the formula

wherein R$_7$ is cyclohex-1,4-dienyl, or an optionally substituted phenyl group represented by the formula

wherein a and a' have the above defined meanings, or R$_7$ is R$_6$ as defined above, and Q is hydroxy, C$_1$-C$_4$ alkanoyloxy, carboxy, sulfo, or amino; or R is a keto group or an oximino-substituted group represented by the formula

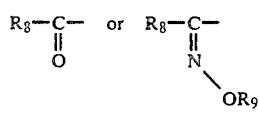

wherein R$_8$ is R$_6$ or R$_7$ as defined above and R$_9$ is hydrogen, C$_1$-C$_4$ alkyl, or a carboxy-substituted alkyl or cycloalkyl group represented by the formula

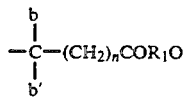

wherein b and b' independently are hydrogen or C$_1$-C$_3$ alkyl, or b and b', when taken together with the carbon to which they are bonded, form a 3-to 6-membered carbocyclic ring, n is 0–3, and R$_{10}$ is hydroxy, C$_1$-C$_4$ alkoxy, amino, C$_1$-C$_4$ alkylamino, or di(C$_1$-C$_4$ alkyl)amino;

R$_2$ is chlorine, bromine, or methyl;
R$_3$ is hydrogen, C$_1$-C$_4$ alkoxy, C$_1$-C$_4$ alkylthio, or formamido; which process comprises contacting a substrate of the formula

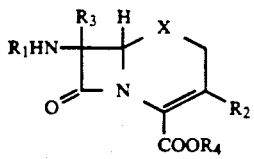

wherein

R₄ is methyl or ethyl; with LiI in a reaction mixture containing a substantial concentration of acetonitrile.

2. The process of claim 1 for preparing a compound of the formula (I) wherein $R_1$ is phenylglycine or substituted phenylglycine.

3. The process of claim 1 for preparing a compound of the formula (I) wherein $R_1$ is phenoxyacetyl.

4. The process of claim 1 for preparing a compound of the formula (I) wherein $R_1$ is thienylacetyl.

5. The process of claim 1 for preparing a compound of the formula (I) wherein $R_1$ is hydrogen.

6. The process of claim 1 for preparing a compound of the formula (I) wherein $R_1$ is 2-(2-thienyl)-2-ethoxyimino-acetyl.

7. The process of claim 1 for preparing a compound of the formula (I) wherein $R_2$ is chlorine.

8. The process of claim 3 for preparing a compound of the formula (I) wherein $R_2$ is chlorine.

9. The process of claim 1 for preparing a compound of the formula (I) wherein $R_2$ is methyl.

10. The process of claim 1 for preparing a compound of the formula (I) wherein $R_3$ is hydrogen.

11. The process of claim 1 for deesterifying an ethyl ester wherein $R_4$ is ethyl.

12. The process of claim 1 for deesterifying an methyl ester wherein $R_4$ is methyl.

13. The process of claim 1 for preparing a compound of the formula (I) wherein X is $CH_2$.

14. The process of claim 1 for preparing a compound of the formula (I) wherein X is sulfur.

15. The process of claim 1 wherein the reaction medium is substantially pure acetonitrile.

16. The process of claim 1 wherein the reaction medium is comprised of from about 0–20% aprotic solvent and from about 80–100% acetonitrile.

17. The process of claim 16 wherein the reaction medium is comprised of from about 0–20% dimethylsulfoxide and from about 80–100% acetonitrile.

18. The process of claim 16 wherein the amount of lithium iodide is from about 2 mole to about 7 mole per mole of product to be produced.

19. The process of claim 18 wherein the amount of lithium iodide is about 3 mole per mole of product to be produced.

20. The process of claim 18 for preparing 7-((phenoxyacetyl)amino)-3-chloro-3-cephem-4-carboxylic acid lithium salt, 7-((phenoxyacetyl)amino)-1-carba-(dethia)-3-chloro-3-cephem-4-carboxylic acid lithium salt, 7-((phenylglycyl)-3-chloro-3-cephem-4-carboxylic acid lithium salt, or 7-((phenylglycyl)amino)-1-carba(dethia)-3-chloro-3-cephem-4-carboxylic acid lithium salt.

* * * * *